(12) United States Patent
Kopecek et al.

(10) Patent No.: US 7,179,487 B1
(45) Date of Patent: Feb. 20, 2007

(54) HYDROGELS OF WATER SOLUBLE POLYMERS CROSSLINKED BY PROTEIN DOMAINS

(75) Inventors: Jindrich Kopecek, Salt Lake City, UT (US); Russell Stewart, Salt Lake City, UT (US); Karin Caldwell, Salt Lake City, UT (US); Chung Wang, Salt Lake City, UT (US); Chih-Hu Ho, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/336,259

(22) Filed: Jun. 18, 1999

Related U.S. Application Data

(60) Provisional application No. 60/089,062, filed on Jun. 19, 1998.

(51) Int. Cl.
*A61K 9/00* (2006.01)
*A61K 38/03* (2006.01)
*A61K 38/16* (2006.01)

(52) U.S. Cl. .................. 424/484; 424/486; 530/300; 514/2; 514/42; 514/44

(58) Field of Classification Search ........... 424/484, 424/486; 530/300; 514/2, 42, 44
See application file for complete search history.

(56) References Cited

U.S. PATENT DOCUMENTS

| | | | | |
|---|---|---|---|---|
| 4,925,677 A | | 5/1990 | Feijen | 424/484 |
| 5,733,563 A | * | 3/1998 | Fortier | 424/422 |
| 5,750,585 A | | 5/1998 | Park et al. | 521/143 |
| 6,004,583 A | | 12/1999 | Plate et al. | 424/486 |

OTHER PUBLICATIONS

W. French Anderson, *Human Gene Therapy*, Nature, vol. 392, Apr. 1998, pp. 25-30.

* cited by examiner

*Primary Examiner*—Anish Gupta
(74) *Attorney, Agent, or Firm*—Thorpe North & Western, LLP

(57) ABSTRACT

A stimuli-responsive, hybrid hydrogel wherein the bulk of the polymer is made up of relatively inexpensive water soluble polymer strands crosslinked by protein domains. The responsiveness of the gel is controlled or modulated by the protein component.

The physical and biological properties of the hydrogel are determined by specifically designed or engineered protein domains.

The crosslinking of the protein domains to the water soluble polymers is by means of non-covalent bonding such as chelation or coordination bonding, biotin-avidin bonding, protein—protein interaction and protein-ligand interaction, or by means of covalent bonding. Methods of making and using the polymer-protein hydrogels are disclosed in this application.

41 Claims, 4 Drawing Sheets

HYDROGELS OF WATER SOLUBLE POLYMERS CROSSLINKED BY PROTEIN DOMAINS

This application claims the benefit of U.S. Provisional Application No. 60/089,862 filed Jun. 19, 1998.

This invention relates to the high-molecular weight crosslinked hydrogel structures formed by crosslinking water soluble polymers with protein domains. More particularly, this invention relates to hydrogel structures having material characteristics such as viscosity, gelation temperature, swelling, elasticity, rigidity, porosity, biodegradability, and bioerosion that can be precisely controlled by manipulating the amino acid sequence, length, and other characteristics of the crosslinking protein domains. Such hydrogels respond to chemical and/or physical stimuli such as pH, temperature, and ionic strength and have utility as drug delivery systems. Such utility can be provided both by the drug carrying capability of the hydrogels as well as the hydrogels themselves that are engineered to contain specific therapeutic crosslinking protein domains.

BACKGROUND OF THE INVENTION

Hydrogels are three-dimensional polymer networks capable of swelling in excess aqueous solution. Stimuli-responsive hydrogels, or "smart hydrogels", undergo large changes in volume in response to physical or chemical changes in their environment. A number of hydrogels have been developed that are responsive to changes in pH, ionic strength, biochemicals, solvents, temperature, electric and magnetic field and light. Tanaka, Phase transitions of gels in Polyelectrolyte Gels: Properties, Preparation, and Applications, 480 ACS Symposium Series (1992). They have important applications as biomaterials, such as contact lenses, soft tissue prostheses and controlled delivery systems for drugs. Furthermore, applications of stimuli-responsive hydrogels include mechanochemical transducers that can be used as switches, microactuators, and as a type of artificial muscle. Although the number and diversity of existing hydrogels are impressive, they have been developed using a relatively small number of polymers and their derivatives, and conventional methods of chemical or physical crosslinking agents. Their functions and biocompatibility are often compromised since their structures are not well defined.

Proteins are becoming increasingly important because of their biological properties. Water-soluble polymers have been crosslinked with molecules of biological origin, such as oligopeptides, oligodeoxyribonucleotides, or intact native proteins. Subr, V. et al. Release of macromolecules and daunomycin from hydrophilic gels containing enzymatically degradable bonds. 1 J. Biomater. Sci. Edn, 261–278 (1990); Obaidat, A. A. & Park, K. Characterization of glucose dependent gel-sol phase transition of the polymeric glucose-concanavalin A hydrogel system. 13 Pham. Res. 989–995 (1996) However, very often there are several factors limiting and influencing the relationship between structure and properties of the hydrogel system, making it difficult to engineer hydrogels with specified responses to particular stimuli.

Bio-engineering techniques provide the ability to modify or synthesize proteins by means of genetic engineering to provide peptide sequences exhibiting desired biological or pharmacological properties as well as having desired physical characteristics due to their coiled or folding nature. Rapidly developing genetic engineering technology makes it possible to produce protein domain-based biomaterials with exact control over their structures through manipulating the DNA sequence encoding the protein structure.

Therefore, it is a significant advance in the art of hydrogels to provide a method to vastly increase the inventory of materials available for rational design of hydrogels. It is also highly desirable to provide a class of hydrogels having material characteristics such as viscosity, gelation temperature, swelling, elasticity, rigidity, porosity, biodegradability, bioerosion that can be precisely controlled and that are responsive to chemical and/or physical stimuli such as pH, temperature, and ionic strength.

This application provides such hydrogels by combining common synthetic polymers crosslinked by protein domains. Protein domains are a class of polypeptides or units of protein structure which are independently and stably folded structure. By manipulating the type, number, and arrangement of protein domains crosslinking the water soluble polymers, it is possible to control the mechanical properties of the hydrogel, such as strength and elasticity; or to give the gel new, or more pronounced, or controlled responses to environmental stimuli. In addition, by adjusting the amino acid sequence of the cross linking protein domains, it is possible to fine-tune the material properties of the gel for specific applications.

OBJECTS AND BRIEF SUMMARY OF THE INVENTION

It is an object of this invention to provide stimuli-responsive hydrogels by combining common synthetic water soluble polymers with natural or biologically-derived protein domains.

Another object of the invention is to provide such hydrogels wherein the polymer is made up of relatively inexpensive water soluble polymer strands crosslinked by protein domains wherein the responsiveness of the gel is controlled or modulated by the protein domain component.

A still further object is to provide hydrogels that have physical and biological properties determined by specifically designed engineered protein domains.

These and other objects are accomplished by providing a composition comprising a polymeric network consisting essentially of, by weight, a water soluble polymer crosslinked by a recombinant protein domain. The composition swells in aqueous solution and forms a three dimensional hydrogel. The properties of the hydrogel are determined primarily by the specific protein domain utilized in the formation of the hydrogel network structure. The crosslinking of the protein domains to the water soluble polymers is by means of chelation or coordination bonding, or by means of covalent bonding. Methods of making and using the polymer-protein domain hydrogels are disclosed in this application.

By proper selection of both water soluble polymers and crosslinking protein domains, stimuli sensitive properties can be incorporated into the hydrogel. Such properties include sensitivity to pH and gelation temperature, elasticity, rigidity, porosity, swelling, viscosity, biodegradability, bioerosion and the like.

While this invention is directed to the development of a novel hybrid hydrogel using any appropriate natural or synthetic protein domain, it is particularly directed to the use of genetically engineered protein domain having coiled-coil structure to crosslink water soluble polymers.

DETAILED DESCRIPTION OF THE INVENTION

Figure 1:
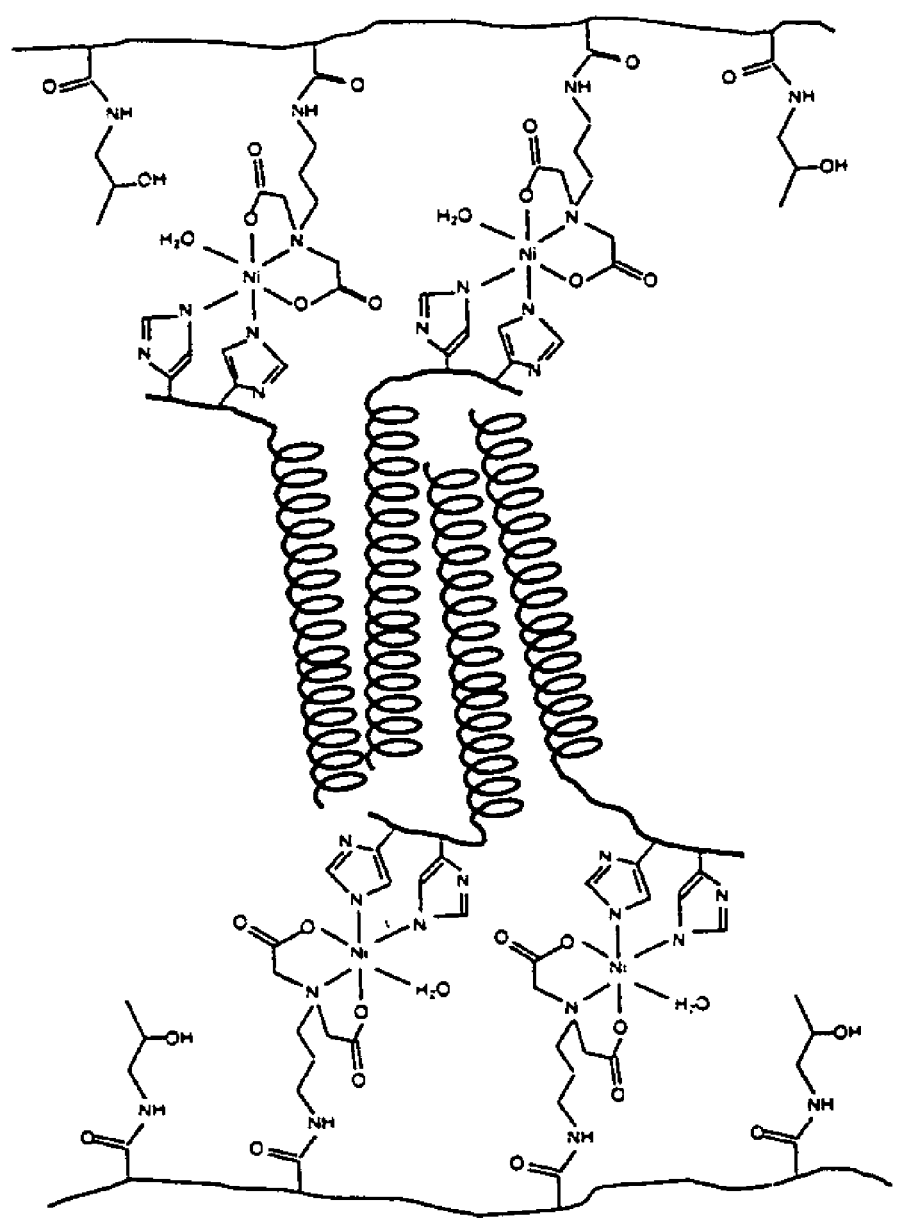
FIG. 1. Shows a schematic illustration of hybrid hydrogel system—coiled-coil protein domains are used to crosslink synthetic polymers. Poly(HPMA-co-DAMA) is shown as the primary chain. A tetrameric coiled-coil (not drawn to scale), consisting of two parallel dimers associating in an anti-paralleled fashion, is shown as an example of many of the possible conformations.

Before the present stimuli-responsive hydrogels and the methods of making and using thereof are disclosed and described, it is to be understood that this invention is not limited to the particular embodiments, process steps, and materials disclosed herein as such embodiments, process steps, and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a protein" includes reference to two or more proteins, reference to "a chemical agent" includes reference to one or more of such chemical agents that may be the same or different chemical agents, and reference to "a polymer" includes reference to two or more polymers.

In describing and claiming the present invention, the following terminology will be used in accordance with the definitions set out below.

As used herein, "protein domain" means peptides of any length and proteins whose structures are independently and stably folded and their structure and properties can be recombined, modified and produced using tools of molecular biology. The terms "polypeptide" and "oligopeptide" are used herein without any particular intended size limitation, unless a particular size is otherwise stated. It is also well understood by the skilled artisan that inherent in the definition of a biologically functional equivalent protein or peptide is the concept that there is a limit to the number of changes that may be made within a defined portion of the molecule and still result in a molecule with an acceptable level of equivalent biological activity. It is well understood that where certain residues are shown to be particularly important to the biological or structural properties of a protein or peptide, e.g. residues in active sites, such residues may not generally be exchanged.

By "coiled-coil protein domain", is meant a common protein folding motif that consists of two or more amphipathic right-handed α-helices winding together into a "knobs-into-holes" fashion forming a slightly left-handed super-helix. Adamson et al., 4 Current Opinion in Biotechnology, 428–437, (1993). Various models of coiled-coils have been designed and characterized. Some have been used to build highly avid mini-antibodies, Pack et al., 264 J. Mol. Biol., 28–34, (1995); epitope-displaying scaffolds, and other novel chimeric proteins. Myszka et al., 33 Biochem. 2363–2372, (1994); Waterman et al., 56 Cancer Research., 158–163 (1996).

"Solution," "aqueous solution" and the like, when used in reference to a combination of drug and water soluble polymers crosslinked by proteins, shall mean a water based solution having such drug/polymer/protein composition dissolved or uniformly suspended therein at a functional concentration.

"Gel" or "hydrogel" or any other similar term shall mean a three dimensional polymeric network formed by an aqueous combination of the polymeric network consisting essentially of a water soluble polymer and a crosslinking protein. A drug may be homogeneously contained in the solution or gel.

"Gel/sol transition" shall mean the condition, e.g. certain pH, temperature, or ion concentration, at which an aqueous combination of the polymer/protein network undergoes a phase transition between a gel and a solution. In response to certain stimuli, such as change of certain pH, temperature, or ion concentration, the gel/sol transition occurs. By manipulating the type, number, and arrangement of protein domains crosslinking the bulk polymer, it is possible to control the mechanical properties of the hydrogel, such as strength and elasticity; or to give the gel new, or more pronounced, or controlled responses to environmental stimuli. In addition, by adjusting the amino acid sequence of the protein domain, it is possible to fine-tune the material properties of the gel for specific applications.

By the term "bioactive agent" or "drug", is meant any chemical material or compound having a desired biological activity or pharmacological effect. In general, this includes therapeutic agents in all of the major therapeutic areas including, but not limited to, anti-infectives, antidiarrheals, antihistamines, anti-inflammatory agents, antineoplastics, antiparkinsonism drugs, antipuritics, antipsychotics, cardiovascular preparations including calcium channel blockers, beta-blockers, antiarrythmics, antihypertensives, vasodilators including general coronary, peripheral and cerebral, central nervous system stimulants, decongestants, diagnostics, hormones, immunosuppressives, muscle relaxants, parasympatholytics. It also includes bioactive macromolecules such as peptides, polypeptides, nucleic acids.

This invention discloses stimuli-responsive hydrogels wherein the polymer is made up of relatively inexpensive water soluble polymer strands crosslinked by protein domains wherein the responsiveness of the gel is controlled or modulated by the protein component. While any types of natural or synthetic protein domains, such as the elastic muscle protein, titin, can be utilized as crosslinking agents, this invention is particularly directed to the use of genetically engineered coiled-coil protein domains to crosslink water soluble polymers. Coiled-coils are formed by association of 2, 3, 4 or more α-helical protein segments into an extended super-helical structure.

Whether it is in the form of a coiled-coil protein domain or any other, by manipulating the type, number and arrangement of the crosslinking protein domains, it is possible to control, not only the biological properties of the domains, but also physical properties of the gel that is formed such as strength, elasticity, and response to environmental stimuli. In other words, by selecting the domain and adjusting the amino acid sequence, it should be possible to fine tune the biological and material properties of a gel for specific application, such as drug delivery.

The novel aspect of this invention is using protein domains as crosslinking agents to crosslink water soluble polymers. Therefore, any water soluble polymers, with or without side chains, as long as the polymer is capable of being crosslinked by means of coordination or covalent bonding, will be suitable for this invention. Examples of such water soluble polymers which may be used include, but are not limited to, are: copolymers of N-substituted methacrylamides such as N-(2-hydroxypropyl) methacrylamide (HPMA) and N-(N',N'-dicarboxymethylaminopropyl) methacrylamide (DAMA); copolymers of HPMA and N-(3-aminopropyl) methacrylamide or copolymers of N-substituted acrylamides, N,N-disubstituted acrylamides, hydrophilic esters of methacrylic or acrylic acid, N-vinylpyrrolidone, N-acryloylmorpholine, sulfoethylmethacrylate, acrylic and methacrylic acid, di- or tri-block copolymers of polyethylene oxide (PEO) and polypropylene oxide (PPO), i.e. PEO-PPO-PEO, that are often identified by the trade name "Pluronic."

Preferably, the polymer is based on N-substituted methacrylamide selected from the group consisting of N-(2-hydroxypropyl)methacrylamide (HPMA), copolymers of N-(N',N'-dicarboxymethylaminopropyl) methacrylamide (DAMA), and copolymers of HPMA and N-(3-aminopropyl)methacrylamide and the derivatives thereof.

The water soluble polymers are crosslinked by the protein domains by various means. One crosslinking technique is by means of chelation or coordination bonds. The protein domain is engineered to terminate with consecutive histidine residues which can strongly associate with metal ions bound by chelating groups conjugated to the water soluble polymer strands. For example, his-tagged protein may be attached to the polymer through coordination bonds formed between the histidine-tag, Ni(II) ion, and nitrogen-oxygen-donor ligand, such as the iminodiacetate of DAMA, of the polymer side chain. This design has long been the basis of protein purification by immobilized metal affinity chromatography.

Another non-covalent attachment means is to modify a polymer strand by D-biotin plus EDC, or by NHS-biotin to form biotinylated polymers. The crosslinking protein is engineered to contain avidin. Avidin has four binding sites for biotin thereby providing a strong binding site to crosslink the biotinylated polymer strands.

Another non-covalent means of attachment is via protein—protein or protein-ligand interactions. An example is through modification of the polymer chains and protein domains with glutathione transferase (GST)-glutathione, or maltose binding protein (MBP)-maltose.

Polymer strands and protein domains can also be modified to provide for covalent attachment. For example, polymer strands can be modified to contain thiol groups that can form disulfide bonds with the thiol group of cysteine residues of the protein crosslinkers. These bonds can be cleaved by reducing agents and be reformed by oxidation. Polymers, such as copolymers of HPMA (N-(2-hydroxypropyl)methacrylamide) and N-(3-aminopropyl)methacrylamide can be modified by heterobifunctional crosslinkers such as SPDP to form sulfhydryl side-chains. Covalent bonds can be formed either by oxidizing the terminal cysteine of protein crosslinkers or by photosensitized reactions between reactive amino acid residues such as histidine, lysine and tyrosine. The bonding of a protein fragment to a HPMA copolymer via a thioether bond is illustrated by Omelyanenko, et al., 3 J. Drug Targeting, 357–373 (1996). Proteins can also be covalently bonded to terminal hydroxyl groups of the PEO blocks of PEO-PPO-PEO triblock copolymers. Li et al., 7 Bioconj. Chem., 7, 592 (1996).

Preferred means to crosslink polymers with the crosslinking protein domain is by means of chelation or coodination bonds.

The relative amount of crosslinking protein domains to water soluble polymers can vary according to the specific polymer utilized and the protein domain selected. Preferably, the molar ratio of water soluble polymers and protein crosslinkers is within a range of about 1:1 and 1:500. More preferably, the molar ratio of water soluble polymers and protein crosslinkers is within a range of about 1:1 and 1:300.

The potential applications for such hybrid hydrogels are numerous and include all current applications for synthetic and natural hydrogels. One specific area of application is as a carrier vehicle for delivery of proteins and other drugs. Therapeutic proteins can be fused with the coiled-coil crosslinking protein domain by genetic engineering technology and be incorporated into the hydrogels. Alternatively, other drug loading methods can also be used such as physically trapping the drug within the hydrogel network. The fact that no organic solvent is needed for hydrogel preparation is a major advantage for loading protein drugs, because it does not cause protein denaturation thus retaining the biological activities of the drugs. Drug release can be better controlled by well-defined hydrogel structure and drug targeting can be enhanced by incorporating targeting moieties into the system.

This system will cause minimal toxicity and mechanical irritation to the surrounding tissue due to the biocompatibility of the materials and will be completely biodegradable within a specific predetermined time interval. The only limitation as to how much drug can be loaded onto the copolymer is one of functionality. Generally speaking, the drug can make up between about 1 to 70% by weight of the drug polymer combination with ranges of between about 5 to 50% being preferred.

This invention is applicable to the delivery of any drug that is stable in the solution as prepared and that will release from the hydrogel matrix following administration. It would serve no useful purpose to attempt to catalog drugs as it will be readily apparent to those skilled in the art the type of drugs that can be used and minimal experimentation will be required to prove the viability of the invention as to any particular drug or class of drugs. In general, the hydrogels of this invention are preferably used to delivery bioactive agents which have medium or poor water solubility or interact with the gel matrix and medium or high molecular weight. Examples of preferred bioactive agents for this invention are, but not limited to: insulin, calcitonin, growth factors, EPO, cytokines, DNA or RNA molecules, cyclosporin A, cis Pt, camptothecin and vaccines.

In the embodiments exemplified in the following examples, a genetically engineered coiled-coil protein domain is used as a physical crosslinker of a water-soluble synthetic copolymer to form a hybrid hydrogel. The fusion protein attaches to the linear synthetic copolymer through coordination bonds formed among its poly(histidine) tail, Ni(II) ions, and nitrogen-oxygen-donor ligand contained on the polymer side-chain. Other metals such as Cu(II), Ga(II), Zn(II) and others may be used in the place of Ni(II). On the other end of the protein domain, there is an association with another crosslinking protein attached to another polymer strand, thus connecting the two polymer strands together. In other words, crosslinking occurs when the coiled-coil domains of the crosslinkers oligomerize.

A fusion protein containing a homodimeric coiled-coil domain was previously designed, chemically synthesized and characterized. Graddis et al., Biochem., 32, 12664–12671, (1993). FIG. 1 shows a schematic illustration of the hybrid hydrogel system—coiled-coil protein domains are used to crosslink synthetic polymers. In this embodiment, an EK42 fusion protein with the sequence of $(VSSLESK)_6$ with N-terminal $(His)_6$-tag and T7-tag spacer, was cloned, expressed and purified from $E.\ coli$. In other embodiments, heterodimeric coiled-coil protein domains EE42 and KK42 were also designed and cloned as his-tag fusion from $E.\ coli$. A metal chelating monomer N-N',N'-dicarboxymethylaminopropyl) methacrylamide was prepared and copolymerized with hydrophilic N-(2-hydroxypropyl)methacrylamide (HPMA) and the resulting copolymer was crosslinked by the coiled-coil fusion protein to form hydrogels, as illustrated in FIG. 1. These hydrogels are stable in aqueous buffers, and at equilibrium they swell to many times their initial volume.

There are two distinctive features reflected from the overall design of the hybrid hydrogel system of this invention. One is the anchoring of protein domain crosslinkers to synthetic polymer backbones and the other is the interface between the coiled-coil domains of the crosslinking protein domains. Each of the two features offer ample latitude for variability in design which leads to versatility of the hybrid hydrogel system in terms of biomedical applications.

The hybrid hydrogel system described in this application utilizes chelation as the means for attaching the protein crosslinkers to the polymeric backbone. This is accomplished through a series of coordination bonds formed between nitrogen-oxygen-donor ligands of the polymer side-chains, Ni(II) ions, and histidine residues of the protein crosslinkers. Although not as strong as covalent chemical bonds, metal coordination is quite robust when compared to other non-covalent associations such as hydrogen bonding, hydrophobic interaction, ionic interaction and van der Waals forces. In particular, nitrogen-oxygen-donor ligand, such as IDA and NTA have high binding constants toward Ni(II) ions. The obvious advantage of this is providing the hybrid hydrogel with reasonable mechanical strength. Weaker associations may not be sufficient to hold the 3-D hydrogel network against stresses exerted in practical applications, such as in drug delivery systems. On the other hand, like all non-covalent associations, chelation or coordination bonds can be destabilized by variations in temperature and pH, or be disrupted by the presence of stronger competitive ligands such as imidazole and EDTA. This creates potential reversibility that can be exploited in designing stimuli-sensitive reversible hydrogels.

While it is noted that crosslinking of the protein domains can occur by covalent bonding or other binding forces or mechanisms, the driving force of the protein crosslinker association of the above example is primarily the hydrophobic interactions between the hydrophobic residues on each coiled-coil strand. Ionic interactions and hydrogen bonding also play important roles in determining the binding specificity, oligomerization, strand orientation and alignment, and, to a lesser extent, the overall stability of the coiled-coils. Numerous physico-chemical studies of native and de novo designed coiled-coil fragments, as well as the invention disclosed herein, show that coiled-coils can undergo cooperative conformational changes sensitive to external stimuli such as temperature, pH, ionic strength, denaturing agents, and organic solvents. In addition, these changes are found to be reversible as the external stimuli are removed. These properties provide the physical-chemical basis underlying this invention for providing the novel stimuli-sensitive hydrogels where such physico-chemical properties can be controlled by suitably designed coiled-coil crosslinking protein domains.

One distinct advantage that can be attributed to these novel hybrid hydrogels lies in its applicability in biomedicine as a delivery system. Biodegradable and non-biodegradable hydrogels have been used extensively in drug delivery systems for some time. In addition to providing hydrogel networks in which drugs may be physically combined, there lies a need to provide hydrogels that can be applicable to new therapeutic techniques and agents, e.g. recombinant peptides, proteins, oligonucleotides and genes. Such delivery systems need to be designed to cater to the needs of successfully protecting, targeting and delivering such new therapeutic agents. This invention demonstrates the possibility of forming swellable physical hybrid hydrogels using engineered proteins as cross-linking agents to build structural and functional well-defined biomaterials that can have a beneficial effect.

The following examples are illustrative of the hybrid hydrogel which is responsive to the environmental stimuli and the method of making thereof, according to the invention. It is to be understood that while the invention has been described in conjunction with the preferred specific embodiments thereof, that which follows is intended to illustrate and not limit the scope of the invention. Other aspects of the invention will be apparent to those skilled in the art to which the invention pertains.

The source for the material and chemical agents used in the invention are: Chemical competent $E.\ coli$ strains DH5a (library efficiency) for plasmid amplification was purchased from Gibco, and BL21(DE3)pLysS for recombinant protein expression was purchased from Novagen. Bacterial plasmid pRSETB-amp$^r$ was purchased from Invitrogen. Plasmid pACYC-kan$^r$, restriction enzymes, Klenow fragment, T4 polynucleotide kinase, and T4 DNA ligase were all purchased from New England Biolabs. Plasmid preparation and DNA extraction from agarose gels were carried out using kits from Qiagen following the recommended procedures. Ni-NTA immobilized metal affinity resin was also purchased from Qiagen and used for recombinant protein purification. For the synthesis of metal-chelating monomers and copolymers, methacryloyl chloride (MA, redistilled before use), bromoacetic acid, and nickel(II) sulfate hexahydrate were purchased from Fluka-Aldrich. N-(3-aminopropyl)methacrylamide hydrochloride was purchased from Polysciences. All the above chemicals were used as received except MA. All the organic solvents were purchased with the highest purity possible and used as received.

EXAMPLE 1

Construction of Plasmids

All the enzymatic reactions involved in plasmid construction were performed at conditions recommended by the manufacturer of the enzymes used. DNA manipulation was carried out based upon the standard protocols. Kanamycin resistant plasmid pRSETB was generated by the following procedure. The kan$^r$ gene in plasmid pACYC was obtained by digestion with BamHI/XbaI, blunted with Klenow fragments, and ligated into the ScaI site of pRSETB-amp$^r$ resulting in pRSET-kan$^r$. Coexpression plasmid pMON-kan$^r$ was constructed by known procedures.

Figure 2:
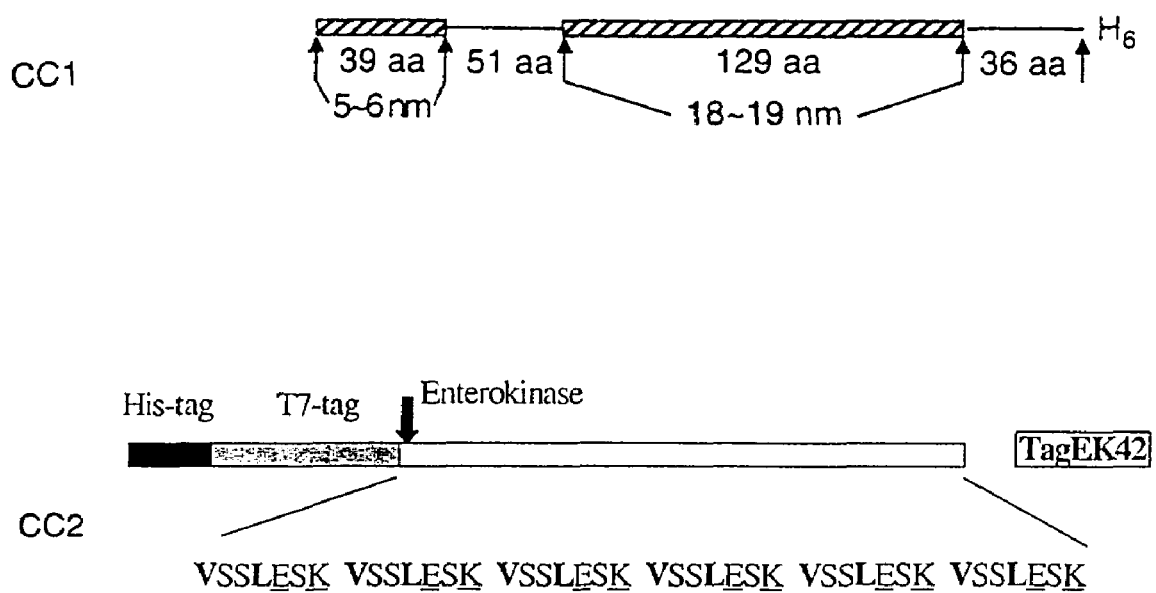
FIG. 2. illustrates the constructions of coiled-coil fusion protein CC1, consisting of a natural protein sequence corresponding to a segment of the stalk region (aa336–590) and CC2, consisting of coiled-coil domain (EK 42, EE42, or KK42), and N-terminal histidine-tag($H_6$) and T7-tag(T7).

FIG. 2 shows DNA sequences encoding coiled-coil domains CC1 and CC2, were designed and flanked by restriction sites used for cloning. This double-stranded DNA was dissected into six single-stranded oligonucleotides, and was synthesized on an automated DNA synthesizer using conventional solid-phase phosphoramidite chemistry. Crude products were dissolved in sterile deionized water and used for cloning without further purification. Concentrations of the oligonucleotides were determined spectrophotometically ($A_{260}$).

Complementary strands of oligonucleotides were mixed pairwise, heated to 92° C. for twenty seconds, and allowed to cool slowly to room temperature forming three duplexes with 5'-overhangs each of twelve nucleotides in length. The same amount of the three duplexes were mixed and ligated into the BamHI/EcoRI sites of pRSETB-kan$^r$. The construct was amplified in DH5a cells, and verified by restriction enzyme digestion testing and direct DNA sequencing.

EXAMPLE 2

Protein Expression and Purification

Co-expression vector pRSETB-kan$^r$-EE42-KK42 was constructed as follows:

The recombinant plasmids were used to transform *E. coli* BL21 (DE3)pLysS cells. The cells were grown in LB medium containing 50 mg/ml Kanamycin and 34 mg/ml chloramphenicol at 37° C. until $A_{600}$ reached 0.6~1. In particular, pMON-kan$^r$-EE42 and pRSETB-amp$^r$-KK42 were used to co-transform host cells, and selected in the presence of the same concentrations of Kanamycin and chloramphenicol plus 50 mg/ml ampicillin. Expression of the target proteins were induced by adding isopropyl β-thiogalactoside to 0.6 mM final concentration followed by incubation for another five hours at 37° C. before cells were harvested. TagEK42 and EE42::KK42 mixtures were purified from the soluble portion of the cell lysate using Ni-NTA immobilized metal affinity resin under native conditions. The target proteins were eluted by 20 mM Tris containing 250 mM imidazole and 500 mM sodium chloride. Eluted proteins were dialyzed against deionized water and lyophilized. Identity and purity of the proteins were assessed by SDS-polyacrylamide gel electrophoresis, amino acid analysis, and MALDI-TOFMS. The apparent molecular mass of TagEK42 and EE42::KK42 in normal aqueous solution (PBS, pH7.3, 25° C.) were determined by size exclusion chromatography (SEC) on a FPLC system (Pharmacia) using a Sephedex-75 (HR10/30) column.

EXAMPLE 3

Circular Dichroism (CD) Characterization of the Coiled Coils

Figure 3:
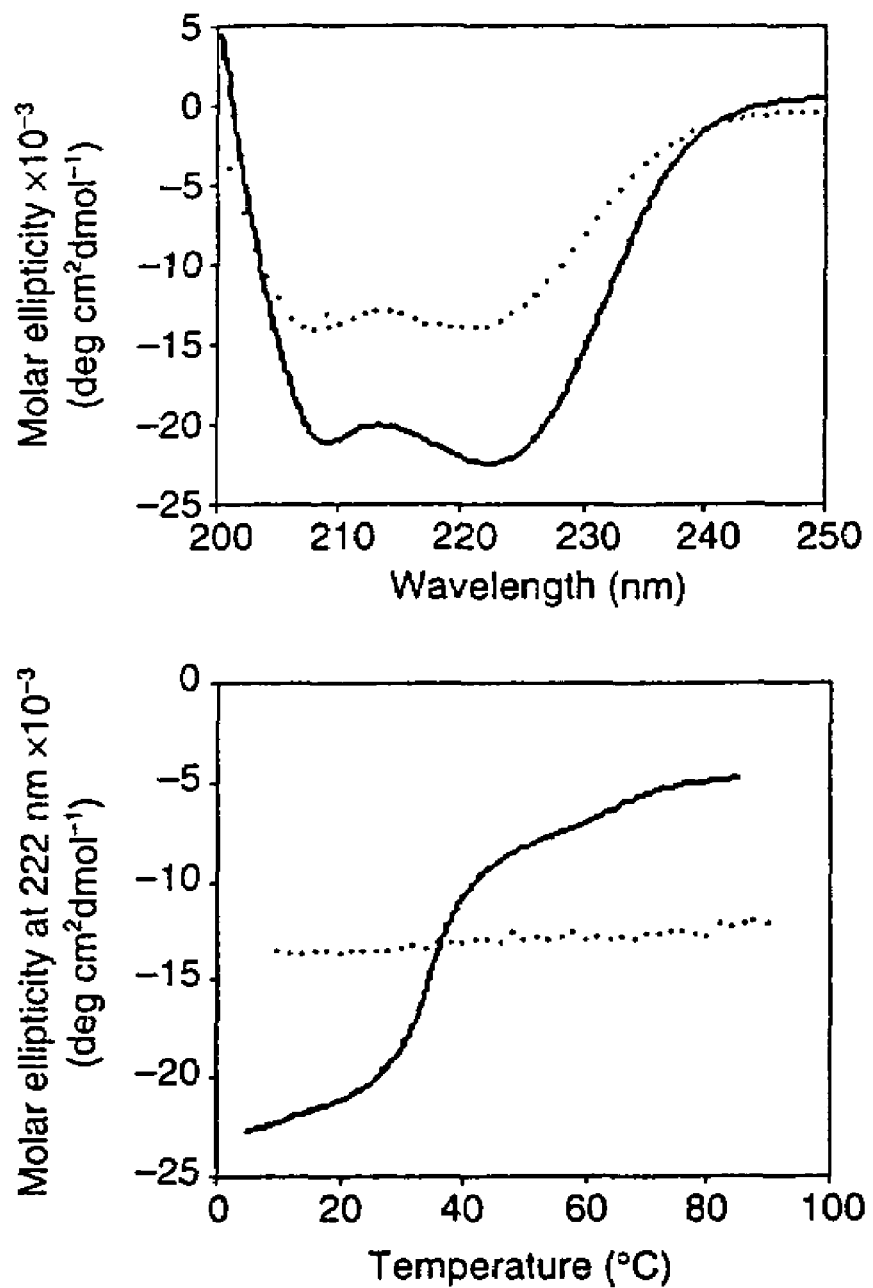
FIG. 3. Shows the circular dichroism (CD) spectrum characterization of coiled-coil fusion protein CC1 (solid line) and CC2 (dotted line). (PBS, pH7.3, 25° C., 1.0 cm length curette, α-helicity+88%, $\emptyset_{222}/\emptyset_{208}$=0.95, protein conc.=18.8 μM determined from $A_{280}$, $\epsilon$=1400 $M^{-1}cm^{-1}$).

Coiled-coil proteins CC1 and CC2 synthesized according to Example 1 and 2 were characterized by circular dichroism. FIG. 3 CD spectra of CC1 or CC2 with different concentrations were recorded at 25° C. in PBS, pH 7.3 using a Jasco J720 CD spectrometer and a 1.0 cm pathlength cell. Protein concentrations were determined from UV absorption at 275 nm (Tyrosine, e=1420 $M^{-1}cm^{-1}$). CD profile of CC1 and CC2 fusion protein is shown in FIG. 3a. The α-helical content was found to be high. The ratio of ellipticities at 220 and 208 nm was calculated to be close to 1. Therefore, the CD profile of CC1 and CC2 indicate that the structure of the protein is predominantly α-helical coiled-coil.

The CD spectrum also showed that CC1 has a major cooperative conformational change at 35° C. and minor one at 65° C. (Bottom of FIG. 3). The CD signal of folded CC1 was fully restored after a temperature cycle, indicating a reversible folding-unfolding process.

The CD spectrum of CC2 also suggested an α-helical coiled-coil conformation. Compared with CC1, the thermal stability of CC2 was unexpectedly high, which may due to the presence of the non-coiled-coil spacer sequence.

EXAMPLE 3

Synthesis of HPMA, DAMA, and MANTA

HPMA was synthesized as described by Strohalm et al., 70 Macromol. Chem., 109–118 (1978). DAMA was synthesized as follows: Bromoacetic acid (14 mmole, 2.0 g) was dissolved in 1 N sodium hydroxide with tiny amount of inhibitor, and cooled to 0~5° C. N-(3-aminopropyl)methacrylamide hydrochloride (7 mmole, 1.25 g) was dissolved in deionized water. Following adjusting pH to 7~9 by 1 N sodium hydroxide, it was added drop-wise into bromoacetic acid solution within 20 min under sufficient stirring. With slight delay, sodium hydroxide (aqueous, 1 N, 14 ml) was also added drop-wise. The reaction was allowed to progress at 0° C. for 2 hrs, and at room temperature for 48 hrs. Under stirring and cooling and the presence of inhibitor the reaction mixture was acidified by adding 1 M hydrochloric acid. Water was removed by evaporation in vacuo using water-bath whose temperature should not exceed 50° C. The residual solid was extracted twice with ethanol (anhydrous, 30 ml each time), and was filtered off. The extract was again evaporated in vacuo to dryness, and extracted twice with acetone (20 ml each time). The remaining solid was filtered off, and dissolved in minimal amount of ethanol (anhydrous, ~500 ml). The product (free acid form of COMII) was crystallized at −20° C. After recrystallization from ethanol (anhydrous), the product was filtered off, washed with diethyl ether (anhydrous), and dried in vacuo. The final yield was 0.5 g (30%). The melting point was found to be 178–180° C. TLC: MeOH, $R_f$=0.45. MW: 258.38 Da. $C_{11}H_{19}N_2O_5$. C %: 51.16 (51.02); H %: 6.98 (7.03); N %: 10.85 (10.72). $^1$H-NMR (DMSO-$D_6$, 200 MHz): d=1.53 (m, 2H, $CH_2$—$CH_2$—$CH_2$—N); d=1.83 (s, 3H, $CH_3$); d=2.63 (m, 2H, $CH_2$—$CH_2$—$CH_2$, —N); d=3.13 (m, 2H, $CH_2$—$CH_2$—$CH_2$—N); d=3.40 (s, 4H, N—($CH_2$ COO)$_2$); d=5.28, 5.61 (d, d, 2H, $CH_2$=); d=7.91 (t, 1H, CO—NH;) d=10~12 (s, 1.4H, (COOH)$_2$)

$N^\alpha,N^\alpha$-bis(carboxymethyl)-$N^\epsilon$-benzoxycarbonyl-L-lysine (Z-NTA) was synthesized from bromoacetic acid and $N^\epsilon$-benzoxycarbonyl-L-lysine. The protecting group Z (benzoxycarbonyl) was then removed by hydrogenation resulting in $N^\alpha,N^\alpha$-bis(carboxymethyl)-L-lysine (NTA) from which MANTA was synthesized as follows. NTA (0.262 g, 1 mmole) was dissolved in sodium hydroxide solution (aqueous, 3 mmole, 5 ml) together with tiny amount of inhibitor, and was cooled to 0° C. To this solution was added methacryloyl chloride (0.048 g, 1.2 mmole), and with slight delay, sodium hydroxide solution (aqueous, 1.2 mmole, 2 ml). Then the reaction was allowed to progress with stirring at room temperature for 2 hrs followed by extraction with equal volume of diethyl ether (anhydrous) to remove unreacted acid chloride. The water layer was acidified to pH2~3 with hydrochloric acid (aqueous, 6M) followed by repeated extraction with ethyl acetate (10 ml per time for 15 times)

while being saturated by sodium chloride solid. Organic layers were combined, and dried over magnesium sulfate (anhydrous) overnight. After the drying agent was filtered off, the organic solvent was evaporated to obtain white solid, which was recrystallized from tetrahydrofuran. About 0.23 g of MANTA was obtained (yield ~70%) with a melting point of 105~107° C. TLC: MeOH/H$_2$0 (4/1), R$_f$=0.72. MW: 330.38 Da. C$_{14}$H$_{22}$N$_2$O$_7$. C %: 50.90 (50.86); H %: 6.71 (6.63); N %: 8.48 (8.41). $^1$H-NMR (DMSO-D$_6$, 200 MHz): d=1.32–1.58 (m, 6H, CH$_2$—(CH$_2$)$_3$); d=1.89 (s, 3H, CH$_3$); d=3.04 (m, 2H, CO—NH—CH$_2$); d=3.32 (t, 1H, CH$_2$—CH (COOH)—N); d=3.46 (s, 4H, N—(CH$_2$—COO)$_2$); d=5.28, 5.60 (t, s, 2H, CH$_2$=); d=7.65 (t, 1H, CO—NH); d=12.40 (s, 2.7H, (COOH)$_3$).

EXAMPLE 4

Synthesis of poly(HPMA-co-DAMA) and poly(HPMA-co-Manta)

Free radical copolymerization of the copolymers was carried out in nitrogen atmosphere for 24 hours at 50 C with methanol (for DAMA) or acetone (for MANTA) as solvent and AIBN as initiator. The copolymers were purified either by repeated precipitation from acetone, or by dialysis against deionized water through a semi-permeable membrane with molecular weight cut-off of 6000~8000 Daltons. Molecular weight distribution was determined by size exclusion chromatography using a FPLC system equipped with Superose 6 column (Pharmacia), and the content of side-chain carboxylic groups was measured by acid-base titration.

EXAMPLE 5

Preparation of Polymer-Ni Complex

Polymer-Ni complexes were prepared by dissolving HPMA copolymers in water and the solution was mixed with ten-times excess of nickel(II) sulfate at pH 7.3 to form 1 to 1 ratio metal complex. Free Ni(II) was separated from polymer-Ni complex using a column packed with Sephadex G-25 gel filtration medium (Pharmacia). Polymer complex was eluted by deionized water and lyophilized. Ni-content was determined spectrophotometrically (A$_{635}$).

EXAMPLE 6

Preparation of Hybrid Hydrogel

Protein crosslinker containing homodimeric coiled-coil domain EK42 was first used to prepare a hybrid hydrogel. An aqueous solution of the fusion protein CC2 was heated to 90° C. for 10 min, mixed with polymer-Ni complex, quickly concentrated under vacuum to 0.5 ml or less, dropped on a Teflon sheet, and dried under normal conditions overnight. The formed thin film was rehydrated and immersed in water containing 100 mM salt. Thin films also formed with control samples containing polymer-Ni alone, TagEK42 alone, and polymer plus CC2, respectively, following the above procedure. However, all the films formed by controls dissolved readily after rehydration, while the film formed by polymer-Ni plus CC1 or CC2 retained its physical integrity. Moreover, the hydrogel formed by polymer-Ni plus CC1 or CC2 swelled in water to almost four times its initial volume. After about 24 hours, the volume of the gel increased even further due to relaxation of the polymer networks. FIG. 1 shows a schematic illustration of the hybrid hydrogel system where coiled-coil protein domains are used to crosslink synthetic polymers, as described above.

EXAMPLE 7

Temperature Responsiveness of the Hybrid Hydrogels

Figure 4:
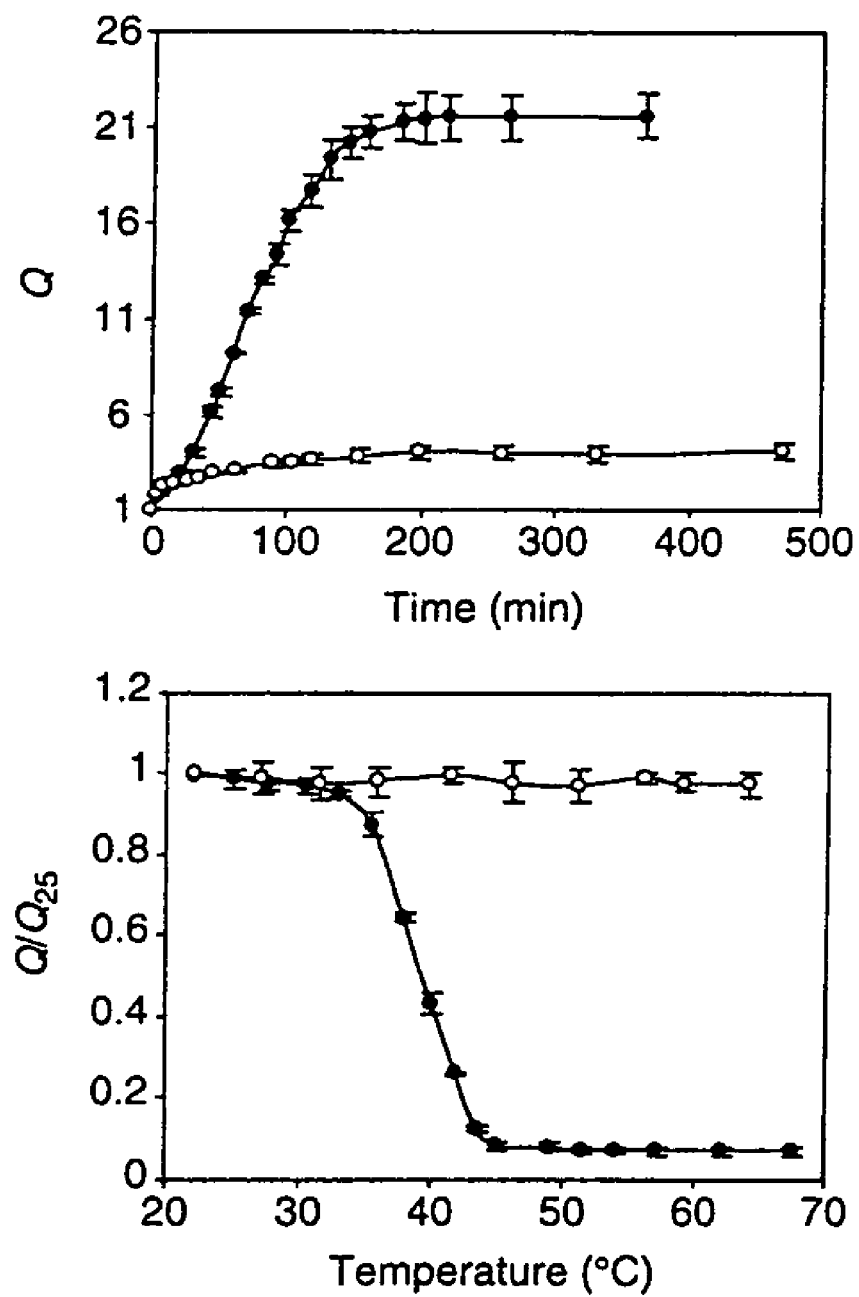
FIG. 4. Shows dynamic swelling and the temperature-induced volume transition of the hybrid hydrogels in PBS.

The temperature-responsiveness of the hybrid hydrogels containing CC1 and CC2 were investigated by measuring dynamic swelling the temperature-induced volume transition of the hydrogels in PBS. The extent of gel swelling was determined by measuring the two-dimensional changes of gel pieces of various shapes. For example, the changes of the three sides of a triangular gel piece were measured based on the optical images taken at a different directions were found to be the same, within experimental error, indicating three-dimensional isotropic swelling of the hydrogel networks. The one dimensional swelling ratio is defined as L/Lo, where L is the size of the swollen gel, and Lo is the corresponding size of the dried gel. L and Lo were determined from optical images of the gels, obtained using a Nikon Eclipse E800 optical microscope, and photographs were taken with a CCD camera. Assuming three dimensional isotropic swelling, the volume swelling ratio Q was calculated as (L/Lo)$^3$. FIG. 4 (top part) shows the dynamic swelling of gel 1 (filled circles) and gel 2 (open circles).

FIG. 4 (bottom part) showed the effect temperature on the gel swelling behavior. Q/Q25 is the ration of the equilibrium volume swelling ratio of gels at an elevated temperature and the equilibrium volumes swelling ratio at 25° C. in the same buffer. Gels were placed in a curette with a jacket connected to a water bath. The rate of temperature increase was 1° C. min$^{-1}$, with equilibrium time of 2 min. The temperature of the water bath was calibrated by measuring the temperature inside the curette with a thermocouple. The error bars represent the standard deviation of three separate measurements. As shown in FIG. 4, hydrogels containing CC1 and CC2 exhibited different thermal stability in solution. On an increase in temperature from 25° C. to 70° C., gel 1 underwent a sudden collapse to 10% of its equilibrium volume at 25° C., with a mid-point transition temperature of 39° C. This mid-point transition temperature of gel collapse was in good agreement (within 5° C.) with the T$_m$ of the main coiled-coil region of CC1 as determined by CD. In contrast, no change in swelling was observed for gel 2 over 25° C. to 70° C., as expected from the CD melting data for CC2 in solution.

As noted above, the hydrogels formed by the hydration of the protein crosslinked water soluble polymers can be loaded with drugs. The protein crosslinkers can be selected or engineered to possess a desired bioactive property. In addition, a drug can be physically loaded and trapped within the three dimensional crosslinked polymer network. Combinations of drugs in the form of protein crosslinkers and physically trapped drugs may also be utilized.

When administered to a human or other warm-blooded animal, the drugs are released from the hydrogel structure by means of appropriate stimuli as referred above or through the bioerosion or biodegradation of the polymer structure.

These examples are intended to be illustrative, and those skilled in the art will recognize, or be able to ascertain using no more than routine experimentation, many equivalents to the specific embodiments of the invention described herein. Such equivalents are intended to be encompassed by the following claims.

Within the guidelines stated herein, one skilled in the art can determine, without undue experimentation, the appro-

The invention claimed is:

1. A composition comprising a polymeric network consisting essentially of a water soluble polymer crosslinked by a protein domain having a coiled-coil structure, wherein said water soluble polymer is a member selected from the group consisting of copolymers of N-substituted methacrylamides, copolymers of N,N-disubstitued acrylamides, hydrophilic esters of methacrylic or acrylic acid, N-vinylpyrrolidone, N-acryloylmorpholine, sulfoethylmethacrylate, acrylic and methacrylic acid, di-block copolymers of polyethylene oxide (PEO) and polypropylene oxide (PPO), and tri-block copolymers of polyethylene oxide (PEO) and polypropylene oxide (PPO).

2. A composition according to claim 1 wherein the crosslinking of the protein domain to the polymer is by means of non-covalent bonding selected from the group consisting of chelation bonding, coordination bonding, biotin-aviding bonding, protein—protein interaction and protein-ligand interaction.

3. A composition according to claim 2 wherein the crosslinking of the protein domain to the polymer is by means of chelation bonding.

4. A composition according to claim 2 wherein the crosslinking of the protein domain to the polymer is by means of biotin-aviding bonding.

5. A composition according to claim 2 wherein the crosslinking of the protein domain to the polymer is by means of protein—protein interaction.

6. A composition according to claim 2 wherein the crosslinking of the protein domain to the polymer is by means of protein-ligand interaction.

7. A composition according to claim 1 wherein the crosslinking of the protein domain to the polymer is by means of covalent or coordination bonding.

8. A composition according to either claim 2 wherein the protein domain is a recombinant protein domain.

9. A composition according to claim 2 wherein the water soluble polymer is an N-substituted methacrylamide and the derivatives thereof.

10. A composition according to claim 2 wherein the N-substituted methacrylamide is a member selected from the group consisting of N-(2-hydroxypropyl)methacrylamide (HPMA), copolymers of N-(N',N'-dicarboxymethylaminopropyl) methacrylamide (DAMA), and copolymers of HPMA and N-(3-aminopropyl)methacrylamide.

11. A composition according to claim 1 wherein the water soluble polymer is a member selected from the group consisting of di-block copolymers of polyethylene oxide (PEO) and polypropylene oxide (PPO), tri-block copolymers of polyethylene oxide (PEO) and polypropylene oxide (PPO).

12. A composition according to claim 1 wherein the water soluble polymer is copolymer of a member selected from the group consisting N,N-disubstitued acrylamides, hydrophilic esters of methacrylic or acrylic acid, N-vinylpyrrolidone, N-acryloylmorpholine, sulfoethylmethacrylate, acrylic and methacrylic acid.

13. A composition according to claim 1 wherein the molar ratio of the water soluble polymer to the crosslinking protein domain is within a range of about 1:1 to 1:500.

14. A composition according to claim 13 wherein the molar ratio of the water soluble polymer to the crosslinking protein domain is within a range of about 1:1 to 1:300.

15. A composition according to claim 1 further comprising a bioactive agent.

16. A composition according to claim 15 wherein the bioactive agent is an oligo- or poly-peptide.

17. A composition according to claim 16 wherein the peptide is conjugated with the crosslinking protein domain.

18. A composition according to claim 15 wherein the bioactive agent is DNA or RNA.

19. A stimuli responsive hydrogel comprising the composition of claim 1 in a three dimensional aqueous solution swelled state.

20. A stimuli responsive hydrogel according to claim 19 wherein the crosslinking of the protein domain to the polymer is by means of non-covalent bonding selected from the group consisting of chelation bonding, coordination bonding, biotin-aviding bonding, protein—protein interaction and protein-ligand interaction.

21. A stimuli responsive hydrogel according to claim 20 wherein the crosslinking of the protein domain to the polymer is by means of chelation bonding.

22. A stimuli responsive hydrogel according to claim 20 wherein the crosslinking of the protein domain to the polymer is by means of biotin-aviding bonding.

23. A stimuli responsive hydrogel according to claim 20 wherein the crosslinking of the protein domain to the polymer is by means of protein—protein interaction.

24. A stimuli responsive hydrogel according to claim 20 wherein the crosslinking of the protein domain to the polymer is by means of protein-ligand interaction.

25. A stimuli responsive hydrogel according to claim 19 wherein the crosslinking of the protein domain to the polymer is by means of covalent or coordination bonding.

26. A stimuli responsive hydrogel according to either claims 19 or 25 wherein the protein domain has a coiled-coil structure.

27. A stimuli responsive hydrogel according to either claims 19 or 25 wherein the protein domain is a recombinant protein domain.

28. A stimuli responsive hydrogel according to claim 19 wherein the water soluble polymer is an N-substituted methacrylamide and the derivatives thereof.

29. A stimuli responsive hydrogel according to claim 19 wherein the N-substituted methacrylamide is a member selected from the group consisting of N-(2-hydroxypropyl) methacrylamide (HPMA), copolymers of N-(N',N'-dicarboxymethylaminopropyl) methacrylamide (DAMA), and copolymers of HPMA and N-(3-aminopropyl)methacrylamide.

30. A stimuli responsive hydrogel according to claim 19 wherein the water soluble polymer is a member selected from the group consisting of di-block copolymers of polyethylene oxide (PEO) and polypropylene oxide (PPO), tri-block copolymers of polyethylene oxide (PEO) and polypropylene oxide (PPO).

31. A stimuli responsive hydrogel according to claim 19 wherein the water soluble polymer is a copolymer of a member selected from the group consisting N,N-disubstitued acrylamides, hydrophilic esters of methacrylic or acrylic acid, N-vinylpyrrolidone, N-acryloylmorpholine, sulfoethylmethacrylate, acrylic and methacrylic acid.

32. A stimuli responsive hydrogel according to claim 19 wherein the molar ratio of the water soluble polymer to the crosslinking protein domain is within a range of about 1:1 to 1:500.

33. A stimuli responsive hydrogel according to claim 32 wherein the molar ratio of the water soluble polymer to the crosslinking protein domain is within a range of about 1:1 to 1:300.

34. A stimuli responsive hydrogel according to claim 19 further comprising a bioactive agent.

35. A stimuli responsive hydrogel according to claim 34 wherein the bioactive agent is an oligo- or poly-peptide.

36. A stimuli responsive hydrogel according to claim 35 wherein the peptide is conjugated the crosslinking protein domain.

37. A stimuli responsive hydrogel according to claim 34 wherein the bioactive agent is DNA or RNA molecule.

38. A stimuli responsive hydrogel according to claim 34 wherein the bioactive agent is dissolved in an aqueous solution.

39. A stimuli responsive hydrogel according to claim 19 wherein the aqueous solution in an equilibrium swollen state is within a range of between 1 to 99% (w/w).

40. A stimuli responsive hydrogel according to claim 39 wherein the aqueous solution in an equilibrium swollen state is within a range of between 5 to 99% (w/w).

41. A stimuli responsive hydrogel according to claim 40 wherein the aqueous solution in an equilibrium swollen state is within a range of between 10 to 99% (w/w).

* * * * *